United States Patent [19]

Brieaddy et al.

[11] Patent Number: 5,104,897
[45] Date of Patent: Apr. 14, 1992

[54] MEDICAL USES OF HALOGEN SUBSTITUTED DIPHENYLSULFIDES

[75] Inventors: Lawrence E. Brieaddy, Raleigh; Claudia E. B. Hollingsworth; Barrett R. Cooper, both of Durham, all of N.C.

[73] Assignee: Burroughs Wellcome Co., Research Triangle Park, N.C.

[21] Appl. No.: 725,384

[22] Filed: Jun. 28, 1991

Related U.S. Application Data

[63] Continuation of Ser. No. 629,085, Dec. 17, 1990, abandoned, which is a continuation of Ser. No. 533,546, Jun. 5, 1990, abandoned.

[30] Foreign Application Priority Data

June 6, 1989 [GB] United Kingdom ............... 8912971

[51] Int. Cl.$^5$ ...................... A61K 31/10; A61K 31/24
[52] U.S. Cl. ..................................... 514/540; 514/712
[58] Field of Search ................................ 514/540, 712

[56] References Cited

U.S. PATENT DOCUMENTS 4,056,632  11/1977  Mehta et al. ........................ 424/330
4,194,009  3/1980  Molloy et al. ...................... 424/332

OTHER PUBLICATIONS

Benfield et al., Drugs, 32: pp. 481–508, (1986), Fluoxetine—A Review of Its Pharmacodynamic and Pharmacokinetic Properties, and Therapeutic Efficacy in Depressive Illness.

Burrows et al., J. Clin. Phychiatry, 49:8, (Suppl.), Aug., 1988, pp. 18–22, Clinical Effects of Serotonin Reuptake Inhibitors in the Treatment of Depressive Illness.

Ferris et al., The Journal of Pharmacology and Experimental Therapeutics, vol. 181, No. 3, 1972, pp. 407–416, A Comparison of the Capacities of Isomers of Amphetamine, Deoxypipradrol and Methylphenidate of Inhibit the Uptake of Tritiated Catecholamines into Rat Cerebral Cortex Slices, Synaptosomal Preparations of Rat Cerebral Cortex, Hypothalamus and Striatum and into Adrenergic Nerves of Rabbit Aorta.

Patrick et al., The Journal of Pharmacology and Experimetal Therapeutics, vol. 241, No. 1, 1987, pp. 152–158, Pharmacology of the Enantiomers of Threo-Methylphenidate.

Bondinell et al., J. Med. Chem., 1980, 23, pp. 506–511, Inhibitors of Phenylethanolamine N-Methyltrasferase and Epinephrine Biosynhesis, 1. Chloro-Substituted 1,2,3,4-Tetrahydroisoquinolines.

Schindlbaure, Monatshefte fur Chemie, 99, pp. 1799–1807, (1968), Reaktionen mit Dimethylformamid, 1. Mitt.

Primary Examiner—S. J. Friedman
Attorney, Agent, or Firm—Donald Brown; Hannah O. Green; Lawrence A. Nielsen

[57] ABSTRACT

A class of halogen-substituted diphenylsulfide compounds are disclosed which produce a large selective inhibition of serotonin uptake in brain. Such compounds are useful in the treatment of depression, anxiety, obsessive compulsive disorders and substance abuse disorders such as alcoholism.

19 Claims, No Drawings

MEDICAL USES OF HALOGEN SUBSTITUTED DIPHENYLSULFIDES

This is a continuation of copending application Ser. No. 07/629,085 filed on Dec. 17, 1990, now abandoned which is a continuation of copending application Ser. No. 07/533,546 filed on June 5, 1990 now abandoned.

The present invention relates to halogen-substituted diphenylsulfides, processes for their preparation, pharmaceutical formulations containing them, and their use in medicine, in particular, for the treatment of depression.

Certain 2-hydroxymethyldiphenylsulfides with antidepressant activity are disclosed in U.K. Patent Specification 1,561,072 (U.S. Pat. No. 4,056,632). Compounds which inhibit serotonin uptake are described in U.S. Pat. No. 4,194,009. The use of serotonin uptake inhibitors for treatment of depression is discussed by Benfield et al., Drugs, 32, 481 (1986) and Burrows et al., J. Clin. Psychiatry, 49 Suppl, 18 (1988).

The compounds of the present invention selectively inhibit serotonin uptake in brain to a degree which is surprisingly better than the compounds disclosed in U.S. Pat. No. 4,056,632. The compounds of the present invention are therefore useful in the treatment of depression in mammals.

In particular, the present invention is directed to compounds represented by formula (I)

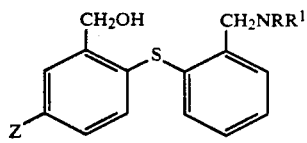

where Z is halo, e.g., fluoro, bromo, iodo, or, preferably, chloro, R and $R^1$ are the same or different and are each hydrogen or straight or branched alkyl of 1 to 6 carbon atoms, most preferably methyl; pharmaceutically acceptable esters; and salts thereof.

Pharmaceutically acceptable esters of formula (I) include carboxylic acid esters in which the non-carbonyl moiety of the ester grouping is selected from straight or branched chain alkyl (e.g., methyl, n-propyl, t-butyl), alkoxyalkyl (e.g., methoxymethyl), aralkyl (e.g., benzyl), aryloxyalkyl (e.g., phenoxymethyl), aryl (e.g., phenyl) optionally substituted by halogen, $C_{1-4}$alkyl or $C_{1-4}$alkoxy, nitro or amino; sulfonate esters such as alkylsulfonyl or alkylarylsulfonyl (e.g., methanesulfonyl or tosylsulfonyl); and amino acid esters such as the aliphatic and aromatic amino acid esters (e.g., Gly, Ala, Val, Leu, Ile, Phe, Tyr and Trp) and other naturally occurring amino acid esters as well as the ester of β-alanine. Pharmaceutically acceptable acid addition salts of the esters are within the scope of this invention and, where the ester moiety itself contains an amino group, diacid addition salts. In the above ester groups, the alkyl groups (including those in alkoxy groupings) contain 1 to 12 carbon atoms, preferably 1 to 4 carbons, and the aryl groups are preferably phenyl or naphthyl.

Acid addition salts of the compounds of formula (I) are within the scope of the present invention. Such salts include those which may be used in intermediate process operations as well as those which are acceptable as final pharmaceutical products. Examples of pharmaceutically acceptable salts of formula (I) are those prepared from e.g., hydrochloric, sulfuric, phosphoric, toluenesulfonic, methanesulfonic maleic, fumaric, tartaric, citric, acetic pamoic, succinic, and nitric acids.

The compounds of formula (I) are serotonin uptake inhibitors as demonstrated by their ability to block the uptake of biogenic amines in rat synaptosomal preparations. The compounds of formula (I) and pharmaceutically acceptable salts and esters thereof are useful in the treatment of depression in mammals, including humans.

The present invention provides a compound of formula (I) or a pharmaceutically acceptable salt or ester thereof for use in medicine. There is further provided the use of a compound of formula (I) or a pharmaceutically acceptable salt or ester thereof in the manufacture of a medicament for treating depression. Additionally, there is provided a method of treating depression in humans which comprises administering to a patient an effective amount of a compound of formula (I) or a pharmaceutically acceptable salt or ester thereof.

Preferred compounds of formula (I) are:

5-chloro-2-((2-((dimethylamino)methyl)phenyl)thio)-benzyl alcohol 5-fluoro-2-((2-((dimethylamino)methyl)phenyl)thio)-benzyl alcohol 5-chloro-2-((2-((methylamino)methyl)phenyl)thio)benzyl alcohol and pharmaceutically acceptable salts and esters thereof, and 5-chloro-2-((2-((dimethylamino)methyl)phenyl)thio)-benzyl acetate The compounds of formula (I) may be synthesized by any method known in the art for making compounds of an analogous structure.

The compounds of formula (I) may be prepared as indicated in the following reaction scheme:

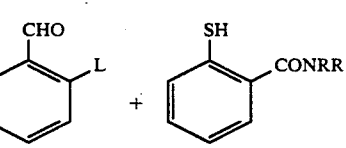

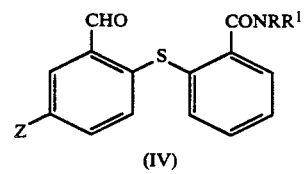

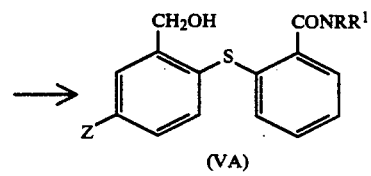

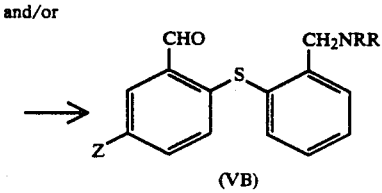

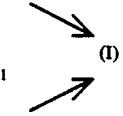

where L is a leaving group, e.g. chloro, and Z, R and $R^1$ are as hereinbefore defined; and optionally forming a pharmaceutically acceptable ester or salt thereof.

The preparation of a compound of formula (IV) may be carried out in a suitable polar solvent, for example, in dimethylformamide, dimethylacetamide or dimethylsulfoxide, in the presence of a base, e.g. potassium carbonate, at a temperature in the range of 20° C. to 200° C.

The reduction of a compound of formula (IV) to the compound of formula (I) may be carried out with a hydride reducing agent, for example, diborane or lithium aluminum hydride at a temperature from 20°–70° C.

The reduction proceeds through the intermediate of formula (VA) and/or (VB) which may optionally be isolated. Preferably however, the reduction of a compound of formula (IV) to a compound of formula (I) is carried out in a single operation.

Compounds of formula (II) may be prepared by oxidation of the corresponding alcohol which may itself be prepared by the reduction of the corresponding carboxylic acid. Compounds of formula (III) may be prepared by amidation of the corresponding commercially available carboxylic acid. Compounds of formula (II) and (III) may be prepared by the methods described in Bondinell et al., J. Med. Chem., 23(5), 506, (1980) and Schindlbauer, Monatsh Chem., 99(5), 1799 (1968).

Compounds of formulae (IV), (VA) and (VB) are novel and represent useful intermediates and are also within the scope of the present invention.

Esters of formula (I) may be prepared by methods well known in the art of organic chemistry, for example, treatment of the alcohol with an acid halide in the presence of an appropriate acid acceptor such as triethylamine.

Acid addition salts may be prepared by reaction with a suitable solvent and the appropriate acid.

Alternatively, compounds of formula (I) may be prepared as indicated in the following reaction scheme:

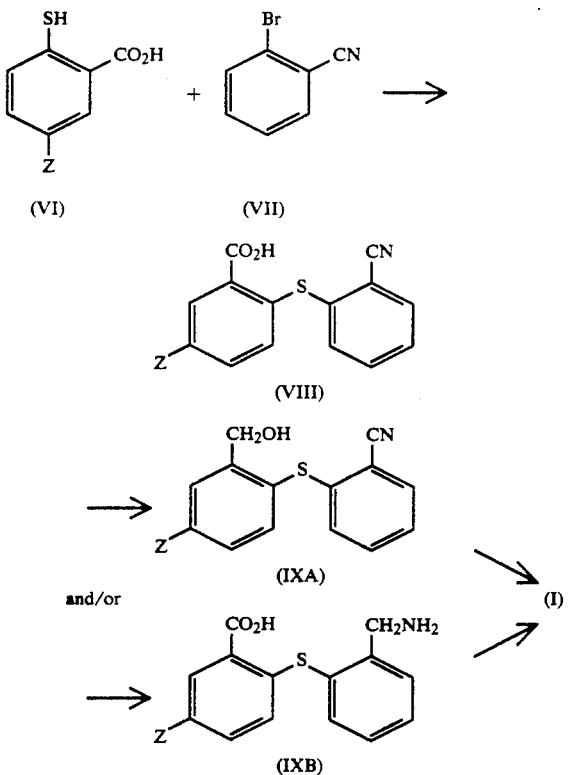

where Z is as defined hereinbefore; and optionally converting the resulting compound of formula (I), wherein R and $R_1$ are both hydrogen, into another compound of formula (I), as defined hereinbefore; and optionally forming a pharmaceutically acceptable ester or salt thereof.

The reaction leading to the compound of formula (VIII) may be carried out in a suitable polar, aprotic solvent such as dimethylformamide or dimethylacetamide, in the presence of an alkali metal lower alkoxide, for example, sodium methoxide or potassium carbonate.

The compound of formula (VIII) may be reduced to a compound of formula (I) using, for example, diborane or lithium aluminium hydride at a temperature from 20° to 100° C. This reduction proceeds through the intermediate compounds of formula (IXA) and/or (IXB) which may optionally be isolated. Preferably, however, the preparation of a compound of formula (I), wherein R and $R^1$ are H, is obtained from a compound of formula (VIII) in a single operation.

The optional conversion of the resulting compound into another compound of formula (I) may be carried out by methods well known in the art of organic chemistry, for example in the case where R and/or R' is methyl, by reaction with an aldehyde such as formaldehyde in the presence of acid, such as formic acid.

Compounds of formulae (VIII), (IXA) and (IXB) are novel and represent useful intermediates and are also within the scope of the present invention.

Pharmaceutically acceptable esters and salts of the compounds of formula (I) may be prepared as described previously.

The compounds of formula (I) and pharmaceutically acceptable esters and salts thereof may be used in treating depression of three main types: neurotic or reactive depression with anxiety, somatic concern and tension; psychotic or endogenous depression with emotional withdrawal, motor retardation, blunted affect, guilt feelings and conceptual disorganization; and a group showing features of both neurotic and psychotic depression with hostility and suspiciousness. Compounds of formula (I) and pharmaceutically acceptable esters and salts thereof may also be used for the treatment of anxiety, obsessive compulsive disorders, and substance abuse disorders such as alcoholism. Compounds of formula (I) and pharmaceutically acceptable esters and salts thereof may also be used to potentiate the analgesic effect of morphine. (See Diagnostics and Statistical Manual of Mental Disorders, third edition,—revised 1987, for descriptions of the above mentioned disorders.)

The compounds of this invention or pharmaceutically acceptable esters or salts thereof may be administered orally, parenterally or rectally.

The preferred antidepressant dosage for parenteral administration of a compound of formula (I) (calculated as the base) is 0.5 mg/kg to 40 mg/kg of mammal body weight per day, and the most preferred dosage is 1 mg/kg to 10 mg/kg of mammal body weight per day.

For the oral and rectal mode of administration, the preferred antidepressant dosage of a compound of formula (I) (calculated as the base) is about 1 mg/kg to 50 mg/kg of mammal body weight per day, while the most preferred dosage (estimated as the base) is 1 mg/kg to 20 mg/kg of mammal body weight per day. A compound of formula (I), or a pharmaceutically acceptable ester or salt thereof, is preferably administered four times daily although the number of daily administrations of the medication and the total dose will vary according to the mammal being treated, and according to the exercise of the physician's discretion.

For example, for the treatment of depression in humans, the preferred unit dosage of a compound of formula (I) or a pharmaceutically acceptable ester or salt thereof (calculated as the base) for oral administration, or administration as a suppository, is about 1 mg to 200 mg, with the more preferred unit dosage being about 5 mg to 100 mg, and the most preferred unit dosage being about 10 mg to 50 mg. All the above doses are given in term of the weight of a compound of formula (I) in the form of its base, but as will be appreciated from the foregoing information, doses are preferably administered in the form of a pharmaceutically acceptable ester or salt.

The preferred dosages for the treatment of anxiety, obsessive compulsive disorders, and substance abuse disorders such as alcoholism are the same as dosages described above for the treatment of depression.

For increasing the analgesic potency of a fixed dose of morphine, the preferred dosage of compounds of formula (I) and pharmaceutically acceptable esters and salts thereof (calculated as the base) is three to four times greater than the dosages required for the treatment of depression.

According to the present invention, in yet another aspect, there is provided a pharmaceutical composition, preferably in unit dosage form, comprising a compound of formula (I), or a pharmaceutically acceptable ester or salt thereof, together with a pharmaceutically acceptable carrier.

A pharmaceutical composition containing a compound of formula (I), or a pharmaceutically acceptable ester or salt thereof, may be presented in discrete units such as tablets, capsules, ampules (i.e., for injection), suppositories or liposomes each containing an effective antidepressant non-toxic amount of the compound and one or more pharmaceutically acceptable carriers.

Conveniently the compound of formula (I) or a pharmaceutically acceptable ester or salt thereof comprises from 5 to 95% by weight of the composition.

The pharmaceutical compositions may be in the form of an oral unit dose preparation for example a cachet, tablet or capsule. Suitable pharmaceutically acceptable carriers for such compositions include solid diluents such as lactose, cornstarch, micronized silica gel, or merely the capsule shell as well as other excipients well known in the art for this purpose.

The pharmaceutical compositions may further take the form of those suitable for rectal use as a suppository with the usual pharmaceutically acceptable carriers such as cocoa butter. Those for parenteral use include an ampule of a sterile solution or suspension with water or other pharmaceutically acceptable liquid as the carrier therefor, or an ampule of a sterile powder for dilution with a pharmaceutically acceptable liquid.

It should be understood that in addition to the aforementioned ingredients, the pharmaceutical compositions of this invention may include one or more of additional ingredients such as diluents, buffers, flavoring agents, binders, surface active agents, thickeners, lubricants, preservatives, and the like. The compositions may be prepared by admixture of the ingredients, and, if necessary, shaping the resulting mass, and filling into suitable containers.

The following examples are provided by way of an illustration of the present invention and should in no way constitute a limitation thereof.

EXAMPLE 1

Preparation of 2-((4-Chloro-2-formylphenyl)thio)-N,N-dimethylbenzamide

Potassium carbonate (27.6 g) was added to a solution of 2,5-dichlorobenzaldehyde (30.2 g) (Bondinell et al., J. Med. Chem., 23(5), 506 (1980)) and 2-thio-N,N-dimethylbenzamide (Schindlbauer, Monatsh. Chem., 99(5), 1799 (1968)) (36.3 g) in 500 mL of dimethylformamide. The reaction mixture was stirred at 160° C. for four hours, added to 2.5 liters of chilled water and extracted with EtOAc to give 50.2 g of a tan solid. Recrystallization from acetone/hexane mixtures gave 43.5 g (80% yield) of 2-((4-chloro-2-formylphenyl)thio)-N,N-dimethylbenzamide, m.p. 87°–88° C.

Anal. Cald. for $C_{16}H_{14}ClNO_2S$; C, 60.09; H, 4.41; N, 4.38; S, 10.03 Found: C, 60.16; H, 4.42; N, 4.36; S, 9.97.

EXAMPLE 2

Preparation of 5-Chloro-2-((2-((dimethylamino)methyl)phenyl)thio)-benzyl Alcohol 2-((4-Chloro-2-formylphenyl)thio)-N,N-dimethylbenzamide (10.0 g) was dissolved in 80 mL of anhydrous tetrahydrofuran and, under nitrogen, added to 80 mL of 1.0M diborane at room temperature. The reaction mixture was refluxed for 2 hr and then stirred at room temperature for 17 hr. The reaction mixture was treated with 100 mL of 50% HCl, warmed on a steam bath for 1 hr and concentrated in vacuo. Treatment with solid NaOH and extraction with EtOAc gave the free base as a yellow oil. This base was dissolved in ether. To the resulting clear solution was added an excess of ethereal HCl. The resulting hydrochloride salt was recrystallized from MeOH/EtOAc mixtures to give 7.4 g (70% yield) of 5-chloro-2-((2-((dimethylamino)methyl)phenyl)thio)benzyl alcohol hydrochloride, m.p. 176°–177° C.

Anal. Calcd. for $C_{16}H_{18}ClNOS.HCl$; C, 55.81; H 5.56; N 4.07; 59.31; Found: C, 55.73; H 5.59; N 4.06; S 9.25;

HNMR(Me$_2$SO-d$_6$); $\delta$10.98 (S, 1, NH), 6.96–7.93 (m, 7H, aromatic), 5.60 (s, 1, OH), 4.54 (s, 2H, OCH$_2$), 4.42 (s, 2H, NCH$_2$), 2.73 (s, 6H, NMe$_2$).

EXAMPLE 3

Preparation of 2-Carboxy-4-chloro-2'-cyanodiphenylsulfide

2-Bromobenzonitrile (81.2 g) was dissolved in 125 mL of dimethylacetamide and added to a warm solution (80° C.) of 2-thio-5-chlorobenzoic acid (78.3 g) and sodium methoxide (44.8 g) in 700 mL of dimethylacetamide and stirred for 17 hr at 100° C. The reaction mixture was added to 2 liters of chilled water, acidified with concentration HCl, filtered, triturated with 5% NaHCO$_3$, filtered and dried to give 108.7 g (90%) of 2-carboxy-4-chloro-2'-cyanodiphenylsulfide, m.p. 197°–200° C.

EXAMPLE 4

Preparation of 2-Aminomethyl-2'-hydroxymethyl-4'-chlorodiphenylsulfide

2-Carboxy-4-chloro-2'-cyanodiphenylsulfide (40.0 g) was dissolved in 100 mL of tetrahydrofuran and added, under nitrogen, to an ice chilled solution of 156 mL of 1.0M diborane. After complete addition, the reaction was refluxed for 2 hr and then stirred at room temperature for 17 hr. The reaction mixture was treated with 100 mL of 50% HCl, warmed on a steam bath for 1 hr and concentrated in vacuo. After treatment with solid NaOH and extraction with EtOAc, 30.0 g of the free base was obtained as an orange oil. This base was dissolved in ether. To the resulting clear solution was added an excess of ethereal HCl. The hydrochloride salt was recrystallized from MeOH/EtOAc mixtures to afford 35.9 g (82% yield) of 2-aminomethyl-2'-aminomethyl-2'-hydroxymethyl-4'-chlorodiphenylsulfide, m.p. 192°–194° C.

Anal. Calcd for $C_{14}H_{14}Cl$ NOS.HCl; C, 53.17; H, 4.78; N, 4.46; Found: C, 53.15; H, 4.86; N, 4.54.

EXAMPLE 5

Preparation of 5-Chloro-2-((2-((methylamino)methyl)phenyl)thio)benzyl Alcohol

Formic acid (1.5 g, 96%) and acetic anhydride (3.4 g) were mixed and warmed at 60° C. for 2 hr. 2-Aminomethyl-2'-hydroxymethyl-4'-chlorodiphenyl sulfide (7.9 g) in 25 mL of tetrahydrofuran was added and stirred at room temperature for 3 hr. The reaction mixture was diluted with water, basified with 50% NaOH and extracted with EtOAc. After concentration in vacuo, the residue was dissolved in 50 mL of tetrahydrofuran and added to LiAlH$_4$ (1.1 g) in 100 mL of tetrahydrofuran. The reaction was refluxed for 4 hr, cooled, and 120 mL of a saturated aqueous solution of Na$_2$SO$_4$ was added. The organic layer was separated, concentrated and chromatographed on silica gel with MeOH to give the free base (4.0 g). This base was dissolved in ether. To the resulting solution was added an excess of ethereal HCl. Recrystallization of the hydrochloride salt from MeOH/EtOAc mixtures gave 3.1 g (34% yield) of 5-chloro-2-((2-((methylamino)methyl)-phenyl)-thio)benzyl alcohol, m.p. 163°–164° C.

Anal. Calcd for $C_{15}H_{14}ClNO_2S.HCl$; C, 52.33; H, 4.39; N, 4.07; S, 9.31; Found: C, 52.18; H, 4.49; N, 3.98; S, 9.21.

EXAMPLE 6

Preparation of 5-Chloro-2-((2-((dimethylamino)methyl)phenyl)thio)-benzyl Acetate A solution of acetyl chloride (2.5 g) in 50 mL of acetonitrile was added dropwise to a solution of 9.8 g of 5-chloro-2-((2-((dimethylamino)methyl)phenyl)thio)-benzyl alcohol (Example 2) in 25 mL of triethylamine and 200 mL of acetonitrile. The reaction mixture was stirred for 3 hr at room temperature, filtered and concentrated in vacuo to give a yellow oil. This oil was chromatographed on silica gel with EtOAc as the eluent. Concentration of solvents afforded 3.8 g (34% yield) of 5-chloro-2-((2-((dimethylamino)methyl)-phenyl)thio)benzyl acetate as a light yellow oil. Upon standing, oil crystallized to a beige solid, m.p. 41°–44° C.

Anal. Calcd. for $C_{18}H_2OCl$ $NO_2S$; C, 61.79; H, 5.76; N, 4.00; S, 9.17; Found: C, 61.75; H, 5.79; N, 3.95; S, 9.11.

EXAMPLE 7

Preparation of 2-((4-Fluoro-2-formylphenyl)thio)-N,N-dimethylbenzamide

Potassium carbonate (21.3 g) was added to a solution of 2,5-difluorobenzaldehyde (19.8 g) and 2-thio-N,N-dimethylbenzamide (27.9 g) in 500 ml of dimethylformamide. The reaction mixture was stirred at 100° C. for three hours, added to 1.4 liters of chilled water and extracted with EtOAc to get 31.8 g of a red oil. The oil was chromatographed on silica gel with 60% toluene/40% EtOAc to get 21.0 g of a red oil.

EXAMPLE 8

Preparation of 5-Fluoro-((2-((2-dimethylamino)methyl)phenyl)thio)-benzyl Alcohol 2-((4-fluoro-2-formylphenyl)thio)N,N-dimethylbenzamide (21.0 g) was dissolved in 100 mL of anhydrous tetrahydrofuran and, under nitrogen, 120 mL of 1.0M diborane were added at room temperature. The reaction mixture was refluxed for ninety minutes, cooled to room temperature, treated with 200 ml of 50% HCl, warmed on a steam bath for 1 hr and concentrated in vacuo. Treatment with aqueous sodium hydroxide and extraction with EtOAc gave the free base as a yellow oil. The base was dissolved in diethyl ether and acidified with etheral HCl to give a beige solid. The hydrochloride salt was triturated with warm acetone to give 10.9 g (48%) of 5-fluoro-2-((2-dimethylamino)methyl)-phenyl)thio)benzyl alcohol, m.p. 148°–150° C.

Anal. Calcd. $C_{16}H_{18}FNOS$ HCl; C, 58.62; H, 5.84; N, 4.27; S, 9.78. Found: C, 58.67; H, 5.86; N, 4.31; S, 9.70.

EXAMPLE 9

Activity Studies Uptake of $^3H$-Biogenic Amines in Crude Synaptosomal Preparations of Rat Hypothalamus and Striatum.

A 0.5 mL aliquot of a crude synaptosomal preparation prepared according to the technique of Ferris et al., J. Pharm. Exp. Ther., 181, 407 (1972) and Patrick et al., J. Pharm. Exp. Ther., 241, 152 (1987) was incubated in a standard incubation medium containing 10 $\mu$M iproniazid, 1 $\mu$M ascorbate and 0.11M of either [$^3H$]dopamine, [$^3H$]1-norepinephrine or [$^3H$]serotonin. Final volumes were 3 mL.

All incubations were conducted for 3 minutes under an atmosphere of 95% O$_2$-5% CO$_2$. The uptake at 0° C. and 37° C. was determined in each experiment and the difference between the two determinations represented the accumulation of [$^3H$]amine by the temperature-dependent uptake process. Test compounds were dissolved in the standard incubation medium and preincubated with the crude synaptosomal preparation for 5 mintes, before the addition of the labeled substrate.

Reactions were stopped by the addition of 2 mL of ice-cold 0.32M sucrose containing 25 mM Tris buffer, pH 7.4, and rapid cooling in an ice-bath. Samples were centrifuged at 49,600×g for 10 minutes. The resulting pellet was washed with 5 mL of 0.9% saline and again centrifuged. The washed pellet was resuspended in 2 mL of 0.4N perchloric acid and centrifuged to remove the precipitated protein. A 1 mL aliquot of the supernatant was taken for determination of radioactivity.

TABLE I

| | IC$_{50}$ (Molar) for Inhibition of Biogenic Amine Uptake | | |
|---|---|---|---|
| Compound | Norepinephrine | Dopamine* | Serotonin |
| Example 2 | $5.5 \pm 1.0 \times 10^{-8}$ | 15% at $10^{-5}$ | $2.1 \pm 0.4 \times 10^{-9}$ |
| Example 5 | $1.1 \pm 3.9 \times 10^{-7}$ | 38% at $10^{-5}$ | $2.1 \pm 1.0 \times 10^{-8}$ |

*Percent inhibition is mean of triplicate assay with S.E.M. < ±5%.

EXAMPLE 10

Formulations

A. Tablet

| Ingredient | Amount per Tablet |
|---|---|
| A compound of formula (I) (as the base) | 150 mg |
| Lactose | 85 mg |
| Cornstarch | 50 mg |
| Micronized silica gel | 10 mg |
| Polyvinylpyrrolidone | 5 mg |

The lactose, cornstarch and compound of formula (I) are mixed together and granulated with a binder (polyvinylpyrrolidone in an alcoholic solution) to form granules. The granules are passed through a 16-20 mesh screen, then air dried, lubricated with micronized silica gel and compressed into tablets. A film coat may then be applied if desired.

B. Capsule

| Ingredient | Amount per Tablet |
|---|---|
| A compound of formula (I) (as the base) | 150 mg |
| Lactose | 125 mg |
| Cornstarch | 125 mg |

The above ingredients are mixed and filled into a two piece hard gelatin capsule.

C. Parenteral Solution

| Ingredient | Amount per Tablet |
|---|---|
| A compound of formula (I) (as pharmaceutically acceptable salt) | 125 mg (calculated as free base) |
| Sterile water for injections, q.s. to | 1.0 ml |

A pharmaceutically acceptable salt of a compound of formula (I) is dissolved in sterile water under sterile conditions to make 1.0 mL. Such a solution may be packaged in a sealed sterile ampule to provide a unit dose or in a sterile vial for multiple doses. If the formulation is to be packed in a multi-dose container, the addition of a bacteriostat such as 0.2 to 0.5% w/v of phenol is desirable.

D. Suppository 150 mg of the hydrochloride salt of a compound of formula (I) is mixed with 250 mg of softened or salted cocoa butter, and a suppository is formed by chilling and shaping in a mold.

We claim:

1. The method of treating anxiety in a mammal which comprises administering to said mammal an effective anxiety treatment amount of a compound of formula (I)

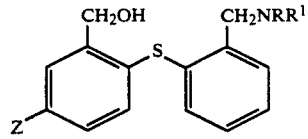

where Z is halo, R and R$^1$ are the same or different and are each hydrogen or straight or branched alkyl of 1 to 6 carbon atoms or pharmaceutically acceptable esters or salts thereof.

2. The method of claim 1 wherein the mammal is a human.

3. The method of treating an obsessive compulsive disorder in a mammal which comprises administering to said mammal an effective obsessive compulsive disorder treatment amount of a compound of formula (I) as defined in claim 1 or a pharmaceutically acceptable ester or salt thereof.

4. The method of claim 3 wherein the mammal is a human.

5. The method of potentiating the analgesic effect produced by morphine in a mammal which comprises administering to said mammal an analgesia potentiating amount of a compound of formula (I) as defined in claim 1 or a pharmaceutically acceptable ester or salt thereof.

6. The method of claim 5 wherein the mammal is a human.

7. The method of treating a substance abuse disorder in a mammal which comprises administering to said mammal an effective substance abuse disorder treatment amount of a compound of formula (I) as defined in claim 1 or a pharmaceutically acceptable ester or salt thereof.

8. The method of claim 7 wherein the mammal is a human.

9. The method of claim 7 wherein the substance abuse disorder is alcoholism.

10. The method of claim 9 wherein the mammal is a human.

11. The method of claims 2, 4, 6, 8 or 10 wherein the compound of formula (I) is 5-chloro-2-((2-((dimethylamino)methyl)phenyl)thio)benzyl alcohol or a pharmaceutically acceptable salt thereof.

12. The method of claim 11 wherein the pharmaceutically acceptable salt is the hydrochloride salt.

13. The method of claim 1, 2, 3, 4, 5, 6, 7, 8, 9, 10, 11, or 12, in which the compound or salt is administered orally.

14. The method of any of claims 1 through 12, in which the compound or salt is administered parenterally.

15. The method of any of claims 1 through 12, in which the compound or salt is administered in a capsule.

16. The method of any of claims 1 through 12, in which the compound or salt is administered as part of a tablet.

17. The method of any of claims 1 through 12, in which the compound or salt is administered as part of an injectable preparation.

18. The method of claim 13, 14, 15, 16 or 17, in which the compound 5-chloro-2-((2-((dimethylamino)methyl)phenyl)thio)benzyl alcohol or a pharmaceutically acceptable salt thereof is administered.

19. The method of claim 18 in which the hydrochloride salt of 5-chloro-2-((2-((dimethylamino)methyl)phenyl)thio)benzyl alcohol is administered.

* * * * *